US00RE34307E

United States Patent [19]

Perry

[11] E Patent Number: Re. 34,307

[45] Reissued Date of Patent: Jul. 6, 1993

[54] DEVICE FOR ORBITAL IMPLANT

[76] Inventor: Arthur C. Perry, P.O. Box 1102, Rancho Santa Fe, Calif. 92067

[21] Appl. No.: 695,607

[22] Filed: May 3, 1991

Related U.S. Patent Documents

Reissue of:

[64] Patent No.: 4,976,731
Issued: Dec. 11, 1990
Appl. No.: 109,505
Filed: Oct. 19, 1987

[51] Int. Cl.[5] ..... A61F 2/14
[52] U.S. Cl. ..... 623/11
[58] Field of Search ..... 623/11, 10, 16, 66

[56] References Cited

U.S. PATENT DOCUMENTS

| | | | |
|---|---|---|---|
| 2,571,721 | 10/1917 | Jardon | 623/4 |
| 2,649,590 | 8/1953 | Cutler | 623/4 |
| 3,436,763 | 4/1967 | Mihauskas | 623/4 |
| 3,480,971 | 12/1969 | Smith | 623/4 |
| 4,087,867 | 5/1978 | Hickmann et al. | 623/4 |
| 4,097,935 | 7/1978 | Jarcho | 623/16 |
| 4,186,448 | 2/1980 | Brekke | 623/16 |
| 4,314,380 | 2/1982 | Miyata et al. | 623/16 |

FOREIGN PATENT DOCUMENTS 0633525 11/1978 U.S.S.R. ..... 623/4

OTHER PUBLICATIONS

Datton, "New eye implant is being tested locally", San Diego Union, Dec. 1985.

A. C. B. Molteno, et al, "Physiological" Orbital Implant, Brit. J. Ophthal., 57, 615-621 (1973).

A. C. B. Molteno, Antigen-Free Cancellous Bone Implants After Removal of an Eye, Trans. Ophthal., Soc., N.Z., 32, 36-39 (1980).

G. C. Sood et al, Human Bone as Buried Implant After Enucleation, Inter. Surgery, 54, 1-3 (1970).

*Primary Examiner*—David Isabella

[57] ABSTRACT

Highly satisfactory orbital comprising granular hydroxyapatite and spheres of porous, low density hydroxyapatite are described. The implants are useful in enucleation and envisceration procedures. In enucleation procedures, the implants can be sutured to the eye muscles by either insertion in a scleral sac or other suitable container or, in the cast of spherical hydroxyapatite, sutured to the eye muscles by means of holes in the spheres. After healing, the implant is drilled to receive a peg for fixing an artificial eye to the implant to complete the prosthesis.

29 Claims, 3 Drawing Sheets

DEVICE FOR ORBITAL IMPLANT

Matter enclosed in heavy brackets [ ] appears in the original patent but forms no part of this reissue specification; matter printed in italics indicates the additions made by reissue.

FIELD OF THE INVENTION

This invention relates to orbital implants following enucleation or evisceration of the eye. In another aspect, it relates to materials for use as orbital implants.

BACKGROUND

Enucleation or envisceration of the eye is performed because of disease or trauma that make the removal of the eye necessary. Following such a procedure, the patient normally desires to have an artificial eye in order to restore a more normal appearance. In order to satisfactorily fit an artificial eye into the orbital socket, an orbital implant must be placed within the orbit to replace the volume within the orbit that was lost when the eye was removed. The use of an orbital implant and the subsequent fitting of the artificial eye confer more than a cosmetic benefit, however. They help maintain the normal structure of the eyelids and eyebrows; they aid in normal tear drainage; and, when used in children, they help stimulate normal growth of the orbital bones.

An early, and still typical, implant is a simple orbital implant in the form of a sphere or globe of plastic or other suitable inert material. When, after surgery, the socket (the area in the orbit that once held the eye) is healed, the socket is fitted with an artificial eye which lies on the tissues that have healed over the implant. Even though an artificial eye can be made today which has a very realistic appearance, the results from the patient's point of view are far from satisfactory. Without attachment of the eye muscles to the artificial eye, the artificial eye drifts within the socket and cannot be made to track with the normal eye. This lack of tracking is quite apparent and disconcerting to even a casual observer, creating a sense of self-consciousness on the part of the patient. As a result of this shortcoming of simple implants, efforts have been made to attach the eye muscles to the implant and then to attach the artificial eye to the implant. This procedure works quite satisfactorily in producing good tracking of the artificial eye. However, the success is short-lived because, in a brief period of time, the implant is extruded from the orbit. The reason for the extrusion of the implant is that the fixing of the artificial eye to the implant material exposes the implant to the outside environment. This permits bacteria to enter and the implant becomes chronically infected. This exposure is necessary, however, to produce the attachment between the implant and the artificial eye.

As previously noted, the typical implant is made of a non-natural material, at least as far as the patient is concerned. Materials that have been used include ivory spheres, gold globes, silk, catgut and a host of other materials. Acrylic plastics or silicones remain the materials of choice, however. To overcome the shortcomings of these materials, it has been proposed to use other more "natural" materials. Among these may be mentioned autoclaved human bone from cadavers, G. C. Sood et al., *International Surgery*, vol. 54, No. 1, p. 1 (1970), and antigenfree cancellous calf bone, so called "Kiel Bone", A.C.B. Molteno, et al., *Brit. J. Opthal.*, vol. 57, p. 615 (1973) and A.C.B. Molteno, *Trans: of the Ophthal. Soc. New Zealand*, vol. 32, p. 36 (1980). Although varying degrees of success have been claimed for these materials, the method of choice remains, to this say, a simple implantation of an orbital implant which is typically made of acrylic, plastic or silicone, even though this deprives the implant of natural movement. No attempt is made to attach the implant to the artificial eye. However, extrusion of the implant is usually avoided and the implants is long-lasting.

As a result of the shortcomings of prior implants, there remains unfilled a long-felt need for an orbital implant which can be readily implanted in a manner which provides tracking of the artificial eye without the eventual extrusion of the implant, a problem which has characterized implants in the past.

SUMMARY OF THE INVENTION AND DESCRIPTION OF PREFERRED EMBODIMENTS

It has been found that the shortcomings of prior implants can be avoided by using sterile hydroxyapatite as the implant material. In a less preferred embodiment of the invention, granular high-density hydroxyapatite, such as that used as a bone grafting material, is used as the implant. This material can be used either to fill a residual scleral sac after an evisceration or, in the case of an enucleation, placed within a scleral sac obtained from a tissue bank, the scleral sac sewn closed and the filled scleral sac used as the orbital implant by being sutured to the eye muscles. Preserved dura or other homologous or autologous collagen graft material may be used in place of the scleral sac. As part of the healing process, the granular material becomes incorporated into the scar tissue and fibrovascular tissue that develops following surgery. After this incorporation occurs, the implant can be drilled or otherwise modified to permit coupling with the artificial eye.

Figure 1:
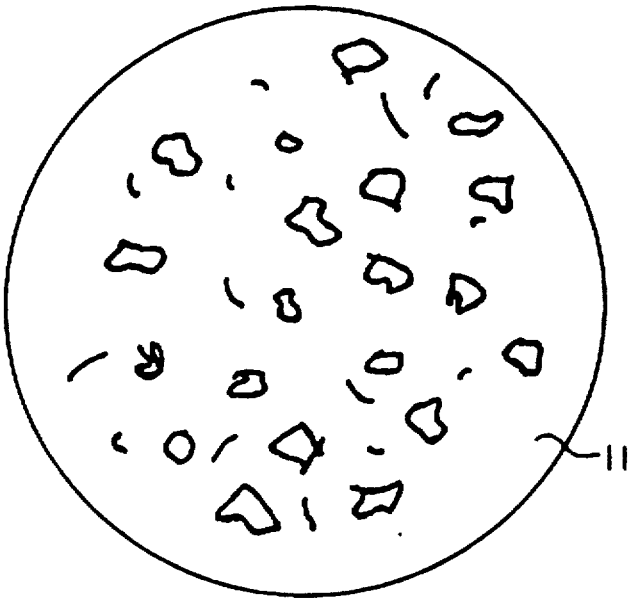
FIG. 1 is a view of a sphere of hydroxyapatite used as an orbital implant according to the present invention.

In a presently more preferred embodiment of the invention, the implant is granular or, preferably, as shown in FIG. 1 a sphere of a low-density, porous hydroxyapatite of the kind obtained from coral or by synthetic means. The sphere is machined to an appropriate size to be used as an implant from a larger block of porous hydroxyapatite. Prior to the use of the implant in the procedure, it is sterilized. If the damaged eye has been eviscerated (all the inner contents removed), the implant is inserted into the remaining scleral sac of the patient's own eye and the scleral sac is sewn closed. If an enucleation is performed (removal of the entire eyeball after severing it from the eye muscles and the optic nerve), the implant can be sewn within a scleral sac, preserved dura or other homologous or autologous collagen graft material. Such tissue is available from eye banks or tissue banks. The muscles which move the eye are attached to the implant by suturing them to the cover material. Alternatively, the implant may be inserted into the orbit without being covered by the graft material and the eye muscles sutured directly into small holes drilled into the implant for that purpose.

Figure 2:
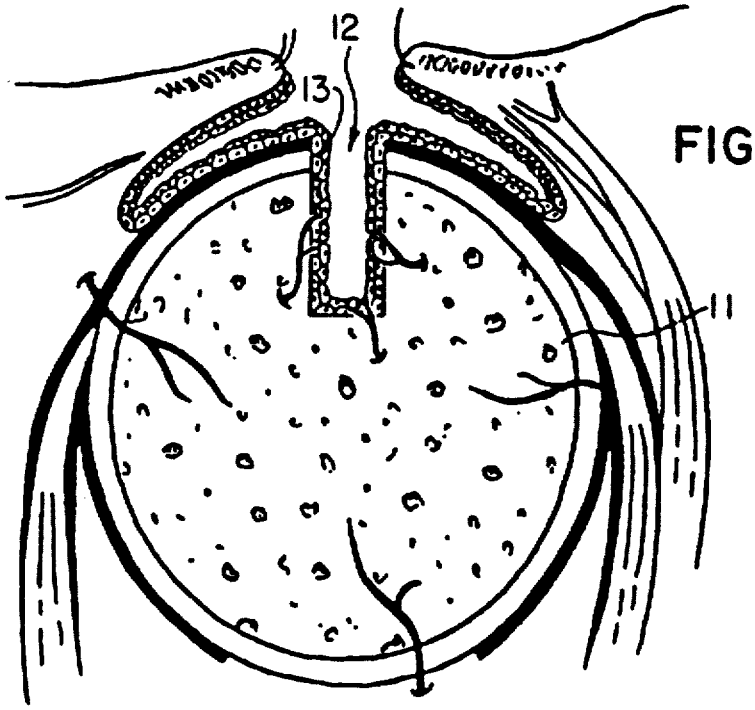
FIG. 2 is a view in cross-section of an orbital implant of the invention after insertion into the eye and after healing has occurred and which has been drilled to received an artificial eye.
Figure 3:
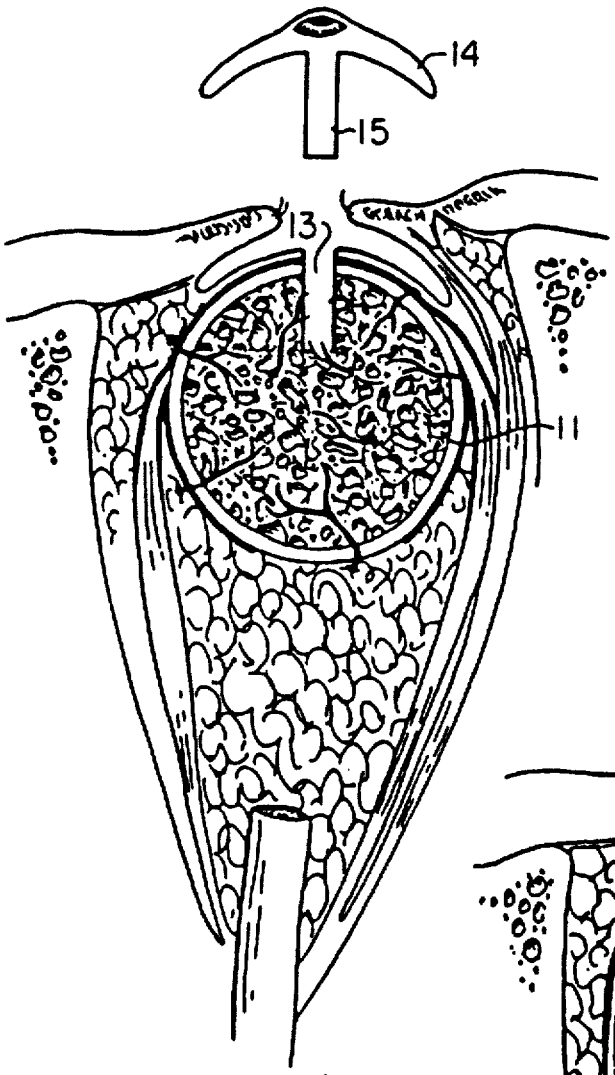
FIG. 3 is a view illustrative of the relationship between an artificial eye useful in the invention and the orbital implant of the invention.

After implantation, the socket is allowed to heal for approximately six months. During the healing process, scar tissue and fibrovascular tissue penetrate the porous structure of the sphere and the implanted scleral sac or other covering is gradually absorbed. After sufficient healing has occurred, the implant can be drilled as shown in FIG. 2 to provide a hole 12 or otherwise modified to permit the artificial eye to be coupled with it. As shown in FIG. 2, tissue also grows into and provides a lining 13 for the drilled hole.

Figure 4:
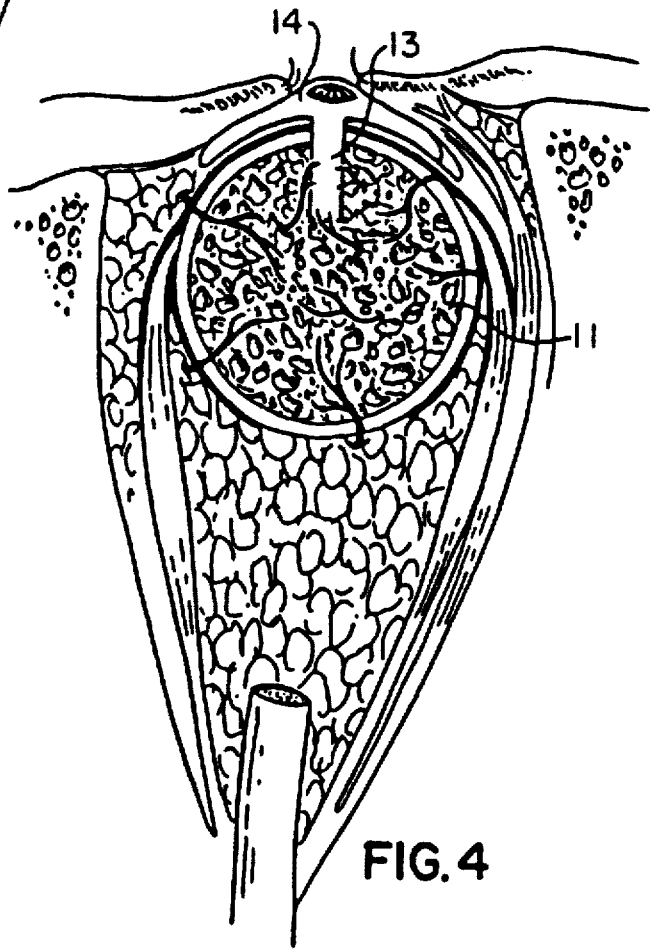
FIG. 4 is a view of the implant and artificial eye of FIG. 3 in which the artificial eye has been inserted into the implant.

In one embodiment of the invention, the artificial eye 14 is permanently fitted with a peg which then fits into the drilled hole 13 of the implant, thus coupling the implant with the artificial eye as shown in FIG. 4.

Figures 5, 6:
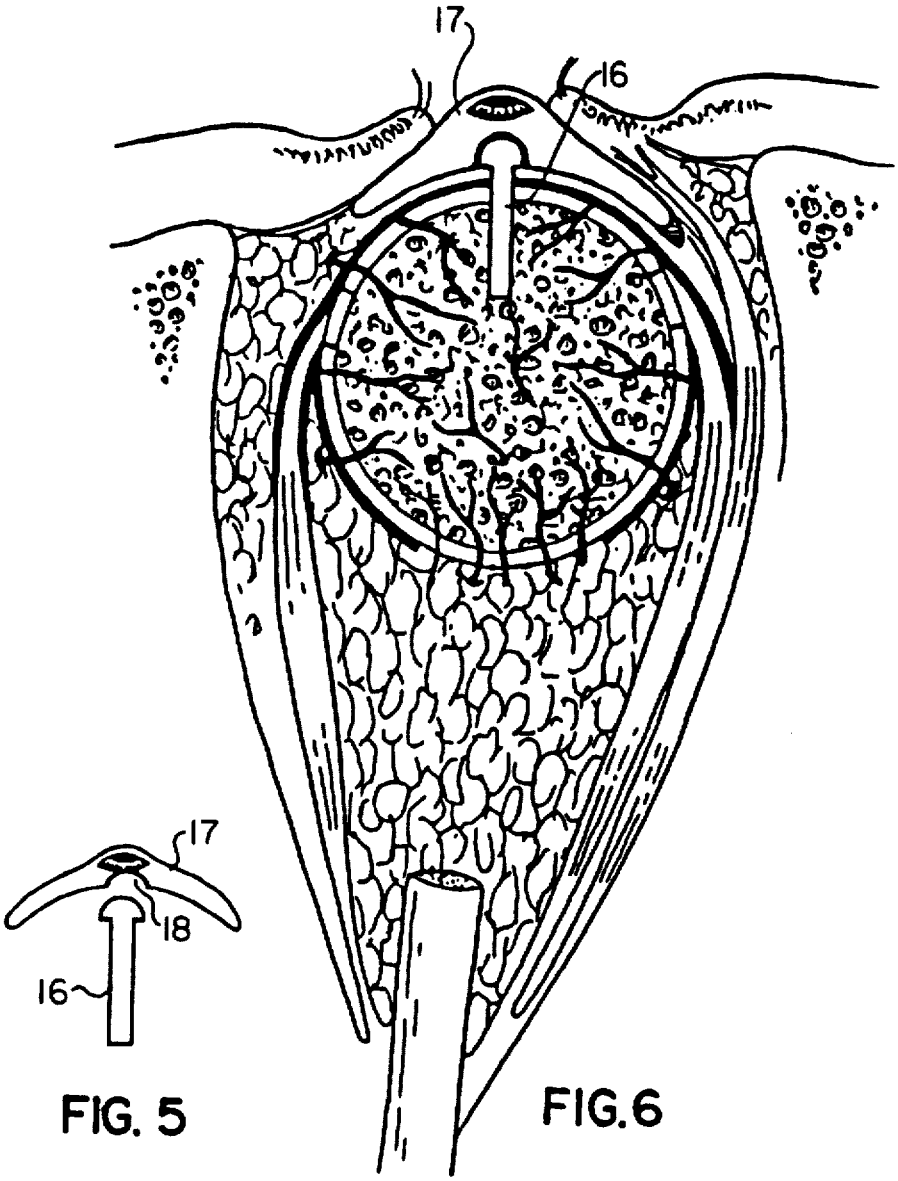
FIG. 5 is a view of an embodiment of an artificial eye useful in the invention.
FIG. 6 is a view of an implant of the invention into which the artificial eye of FIG. 5 has been inserted.

In another embodiment of the invention illustrated in FIGS. 5 and 6, a protruding peg 16 is placed into the drilled hole of the implant and the artificial eye 17 is recessed as at 18 to receive the peg and thus be coupled with the implant via the peg. In either embodiment, the artificial eye and peg can be readily removed to permit cleaning.

The resulting implants are very satisfactory from the patient's point of view. The implant does not extrude from the orbit. Instead, it becomes an integral part of the residual eye structure because of the intrusion of the scar tissue and fibrovascular tissue into the porous material. Being fixed to the eye muscle, the implant is capable of tracking with the normal eye. When an artificial eye is fixed to the implant to complete the prosthesis, a very satisfactory, natural appearance results.

To date, 27 patients have had this material implanted into the orbit. There have been no chronic infections or extrusions of the implant in patients who have had implants for up to 26 months. In those patients who have had the hole drilled into the implant so that it is coupled to the artificial eye, the tracking has been very satisfactory.

We claim:

1. An orbital implant comprising a monolithic sphere of sterile, low density, porous hydroxyapatite of a size suited for insertion into the orbital socket to replace an eye removed therefrom.

2. An implant according to claim 1, wherein the sphere is obtained from coral or other synthetic means.

3. An implant according to claim 1 wherein the material is sewn within a scleral sac, preserved dura, or other homologous or autologous collagen graft material.

4. An implant according to claim 1 wherein the sphere is adapted to receive an artificial eye.

5. An implant according to claim 4 wherein the sphere is provided with a hole to receive a peg for fixing an artificial eye to the implant.

6. An implant according to claim 1 wherein the sphere is provided with holes to permit the direct suturing of eye muscles to the sphere.

7. An implant according to claim 6 wherein the sphere is provided with a hole to receive a peg for fixing an artificial eye to the implant.

8. A prosthesis comprising an orbital implant according to claim 1 to which is fixed an artificial eye.

9. A surgical process comprising evisceration of an eye and filling the scleral sac with a monolithic sphere of sterile, porous, low density hydroxyapatite of a size suited for insertion into the scleral sac to replace the contents of the eviscerated eye.

10. A process according to claim 9 wherein the implant is adapted to receive an artificial eye.

11. A process according to claim 10 wherein the implant is provided with a hole to receive a peg to which is fixed to the artificial eye.

12. A process according to claim 10 wherein the artificial eye is fixed to the implant.

13. A surgical process comprising enucleation of an eye and its replacement by an orbital implant comprising a monolithic sphere of sterile, porous, low density hydroxyapatite of a size suited for replacement of the enucleated eye sewn within a container selected from the group consisting essentially of a scleral sac, preserved dura, homologous or autologous graft material.

14. A process according to claim 13 wherein the container is sutured to the eye muscles.

15. A process according to claim 13 wherein the sphere is provided with holes and, using such holes, sutured directly to the eye muscles.

16. A process according to claim 13 wherein the sphere is sewn within a container selected from a scleral sac, preserved dura or other homologous or autologous graft material and the container sutured to the eye muscles.

17. A process according to claims 13, 14, 15 or 16 wherein the implant is adapted to receive an artificial eye.

18. A process according to claim 17 wherein the implant is provided with a hole to received a peg to which is fixed the artificial eye.

19. A process according to claim 18 wherein the artificial eye is fixed to the implant.

*20. A surgical process comprising filling the scleral sac of an eviscerated eye with a monolithic sphere of sterile, porous, low density hydroxyapatite of a sized suited for insertion into the scleral sac to replace the contents thereof.*

*21. A process according to claim 20 wherein the implant is adapted to receive an artificial eye.*

*22. A process according to claim 21 wherein the implant is provided with a hole to receive a peg to which is fixed the artificial eye.*

*23. A process according to claim 22 wherein the artificial eye is fixed to the implant.*

*24. A surgical process comprising replacing an enucleated eye with an orbital implant comprising a monolithic sphere of sterile, porous, low density hydroxyapatite of a size suited for replacement of the enucleated eye.*

*25. A process according to claim 24 wherein the implant is sewn within a container selected from a scleral sac, preserved dura, homologous graft material or autologous graft material and the container is sutured to the eye muscles.*

*26. A process according to claim 24 wherein the sphere is provided with holes and, using such holes, sutured directly to the eye muscles.*

*27. A process according to claims 24, 25, or 26 wherein the implant is adapted to receive an artificial eye.*

*28. A process according to claim 27 wherein the implant is provided with a hole to receive a peg to which is fixed an artificial eye.*

*29. A process according to claim 28 wherein the artificial eye is fixed to the implant.*

* * * * *